United States Patent [19]

Desmarteau et al.

[11] Patent Number: 5,023,377
[45] Date of Patent: Jun. 11, 1991

[54] PROCESS FOR PREPARING FLUORINATED COMPOUNDS

[75] Inventors: Darryl D. Desmarteau; Stefan P. Kotun, both of Clemson, S.C.; Alessandro Malacrida, Sovico, Italy

[73] Assignee: Ausimont, S.R.L., Milan, Italy

[21] Appl. No.: 387,819

[22] Filed: Aug. 1, 1989

[30] Foreign Application Priority Data

Aug. 2, 1988 [IT] Italy .............................. 21615 A/88

[51] Int. Cl.$^5$ ............................................. C07C 239/20
[52] U.S. Cl. ...................................... 564/301; 568/842
[58] Field of Search ............................................ 564/301

[56] References Cited

U.S. PATENT DOCUMENTS 4,010,212 3/1977 Pavlik .................................. 260/615

OTHER PUBLICATIONS

Encyclopedia of Polymers Sovetskaya Encyclopaedia Publishers 1977, vol. 3, No. 763 (Fragment).
Chemical Abstracts, vol. 93, No. 7, Aug. 18, 1980, p. 904, Abstract No. 70905t (A. Seikiya et al.).

Primary Examiner—Richard L. Raymond
Attorney, Agent, or Firm—Morgan & Finnegan

[57] ABSTRACT

A process for preparing fluorinated compounds belonging to the classes:

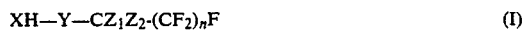

and

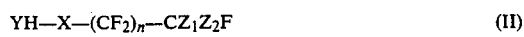

wherein:
X is $NR_x$, O, S, $CFR_x$, $C(R_x)_2$, or $CF_2$;
Y is $NR_x$, O, S, $CFR_x$, $C(R_x)_2$, or $CF_2$;
X is different from Y;
$R_x$ is a perhalogenated alkyl group, containing from 1 to 4 carbon atoms;
n is either 0 or 1;
$Z_1$ and $Z_2$, which may be either equal to, or different from, each other, represent F, Cl, Br, H or $R_x$.

The process is characterized in that a fluorinated cyclic compound of the formula:

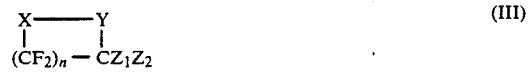

is reacted, at a temperature within the range of from −80° to +300°, with HF in the presence of a Lewis acid. Some of the so-obtained compounds per se are novel.

8 Claims, No Drawings

PROCESS FOR PREPARING FLUORINATED COMPOUNDS

DESCRIPTION OF THE INVENTION

The present invention relates to a process for the preparation of fluorinated compounds, as well as to certain novel fluorinated compounds obtained by said process.

More particularly, the present invention relates to the preparation of fluorinated compounds having the formulae:

$$XH-Y-CZ_1Z_2-(CF_2)nF \qquad (I)$$

and $$YH-X-(CF_2)_n-CZ_1Z_2F \qquad (II)$$

wherein
X is $NR_x$, O, S, $CFR_x$, $C(R_x)_2$, or $CF_2$;
Y is $NR_x$, O, S, $CFR_x$, $C(R_x)_2$, or $CF_2$;
X is different from Y;
$R_x$ is a perhalogenated alkyl group, containing from 1 to 4 carbon atoms;
n is either 0 or 1;
$Z_1$ and $Z_2$, which may be either equal to, or different from, each other, represent F, Cl, Br, H or $R_x$.

An object of the present invention is to provide a process for the production of fluorinated compounds belonging to the classes (I) and (II).

Another object of the present invention is to provide novel fluorinated compounds belonging to the classes (I) and (II).

The first object is achieved by a process, according to the present invention, for preparing fluorinated compounds belonging to the classes:

$$XH-Y-CZ_1Z_2-(CF_2)nF \qquad (I)$$

and $$YH-X-(CF_2)_n-CZ_1Z_2F \qquad (II)$$

wherein X, Y $R_x$, n, $Z_1$ and $Z_2$ have the above stated meanings. This process is characterized in that a fluorinated cyclic compound of the formula:

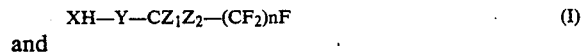

is reacted, at a temperature within the range of from $-80°$ to $+300°$, with HF in the presence of a Lewis acid.

The Lewis acid is preferably selected from $AsF_5$, $SbF_5$, or $BF_3$.

The most preferred Lewis acid is usually $AsF_5$.

At the end of the reaction, the Lewis acid and any excess of HF are separated from the end product, preferably by neutralization with a neutralizing agent.

As the neutralizing agent, e.g., NaF, KF, $KHF_2$, RbF or CsF may be used. The preferred agent is NaF.

The preferred reaction temperature is usually within the range of from 0° to 100° C.

The molar ratio of HF to the fluorinated cyclic compound (III) is usually within the range of from 4 to 50, and preferably from 4 to 25.

The molar ratio of the Lewis acid (computed as $AsF_5$) to the fluorinated cyclic compound (III) is commonly within the range of from 0.1 to 5, and preferably from 1 to 2.

The reaction is usually complete within a time in the range of from 30 minutes to 3 days and, more commonly, within the range of from 1 hour to 36 hours At the end of the reaction, the reaction mixture is preferably treated with a neutralizing agent, in order to neutralize any unreacted HF and the Lewis acid.

This neutralization step may be usually accomplished at a temperature within the range of from $-20°$ to $+50°$ C, and preferably within the range of from $+20°$ to $+25°$ C.

In general, an excess amount of neutralizing agent is used. This excess amount is usually within the range of from 2 to 10 mols of neutralizing agent (computed as NaF) relative to each mol of the sum of the starting HF plus the Lewis acid.

This excess is preferably within the range of from 3 to 5 mols of neutralizing agent relative to the above said sum.

The neutralization step may be commonly carried out within a time in the range of from 30 minutes to 30 days.

In the fluorinated cyclic compound (III) used as the starting material, and in the fluorinated compounds (I) and (II) obtained, $R_x$ is preferably a fluorinated alkyl group.

According to the structure of the starting cyclic compound (III), and, in particular, according to the nature of X and of Y and of the substituents $Z_1$ and $Z_2$, the end compound (I) or the end compound (II) or both of them, are obtained as it will be shown hereinunder relative to specific cases.

In the case of the end compound (II) when X is constituted by $CR_xF$ or $CF_2$, the end product will lose HF to yield the unsaturated compound:

$$Y=CR_x-(CF_2)_n-CZ_1Z_2F$$

or $$Y=CF-(CF_2)_n-CF_1Z_2F$$

According to a preferred form of practical embodiment of the preferred invention, the cyclic compound used as the starting compound is:

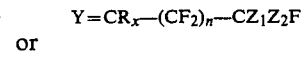

and the end products are: the amines $$R_x-NH-O-CZ_1Z_2-CF_3 \qquad (V)$$

and the hydroxylamines $$R_x-NOH-CF_2-CZ_1Z_2F \qquad (VI)$$

The amines $R_x-NH-O-CZ_1Z_2-CF_3$ (V) are compounds per se novel. They constitute useful intermediates, in particular for the preparation of the corresponding N-fluorinated amines:

$$R_x-NF-O-CZ_1Z_2-CF_3 \qquad (VII)$$

which are suitable as catalysts for the polymerization of $C_2F_4$.

Also the N-fluorinated compounds (VII) are per se novel and have the same utility, and constitute a further object of the present invention.

The N-fluorinated compounds (VII) may be obtained by reaction of the amines:

$$R_x-NH-O-CZ_1Z_2-CF_3 \qquad (V)$$

with $F_2$ at a temperature within the range of from $-195°$ to $5°$ C.

The reaction temperature is preferably within the range of from $-100°$ to $0°$ C. The molar ratio of $F_2$ to the amine is usually within the range of from 1 to 2, and, still more usually, within the range of from 1.0 to 1.3.

The preferred amines (V) and N-fluorinated amines (VII) are those in which $R_x$ is $CF_3$, $Z_1$ is F and $Z_2$ is F, Cl or H.

These preferred compounds are:

$$CF_3-NH-O-CF_2CF_3 \qquad (VIII)$$

1,1,1-trifluoro-N-(pentafluoroethoxy)-methane-amine;

$$CF_3-NH-O-CFCl-CF_3 \qquad (IX)$$

1,1,1-trifluoro-N(1-chloro-1,2,2,2-tetrafluoroethoxy)-methane-amine $$CF_3-NH-O-CHF-CF_3 \qquad (X)$$

1,1,1-trifluoro-N(1-hydro-1,2,2,2-tetrafluoro-ethoxy)-methane-amine $$CF_3-NF-OCF-CF_3 \qquad (XI)$$
1,1,1-trifluoro-N-fluoro-N(pentafluoroethoxy)-methane-amine;

$$CF_3-NF-O-CFCl-CF_3 \qquad (XII)$$

1,1,1-trifluoro-N-fluoro-N(1-chloro-1,2,2,2,-tetrafluoroethoxy)-methane-amine;

$$CF_3-NF-O-CFH-CF_3 \qquad (XIII)$$

1,1,1-trifluoro-N-fluoro-N(1-hydro-1,2,2,2-tetrafluoroethoxy)-methane-amine.

The possibility of obtaining, in some cases, the amines (V), and, in other cases, a mixture consisting of the amines (V) and the hydroxylamines (VI), when as the starting products the cyclic compounds (IV) are used, is illustrated by the following reactions:

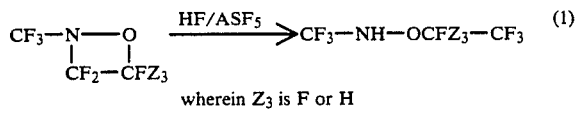

wherein $Z_3$ is F or H

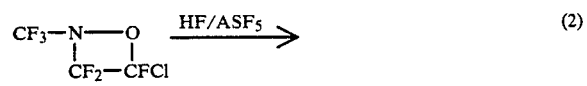

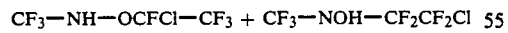

According to another preferred form of practical embodiment of the present invention, the cyclic compound used as the starting material is:

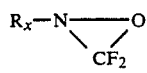

and the end product is $$R_x-NH-O-CF_3 \qquad (XV)$$

According to a further preferred form of practical embodiment of the present invention, the cyclic compound used as the starting compound is:

wherein $R^1$ and $R^2$, either equal to, or different from, each other, are F or $R_x$.

The end product is:

EXAMPLES

The present invention is now still further disclosed in the following examples:

EXAMPLE 1

This example illustrates the reaction:

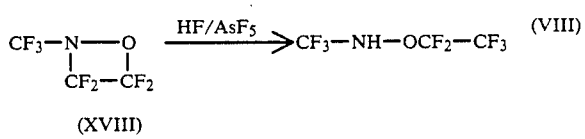

The perfluorinated oxazetidine (XVIII) used as the starting material was prepared from $CF_3-N=O$ and $CF_2=CF_2$ (Barr, D. A. et al., J. Chem. Soc., 1955, 1881-1889).

A reaction vessel was assembled by heat-sealing an end of a Teflon-FEP tube of ⅜″ outside diameter and ¼″ internal diameter.

The other end of the tube was inserted inside a ⅜″ ¼″ stainless-steel reducing union, which was connected in its turn to a stainless-steel valve, through a ¼″-174 ″ stainless-steel reducing port connector.

The internal volume of the reactor was 39.5 ml. An insert of stainless-steel was placed inside the open end of the tubular FEP reactor, to act as a support.

The FEP reactor was evacuated under vacuum (5 microns Hg; all the subsequent manipulations under vacuum were carried out under this pressure), and weighed.

The reactor was cooled down to $-196°$ C., and inside it anhydrous HF was condensed by static vacuum, through a stainless-steel manifold. The reactor was heated up to $23°$ C., and was weighed again; the amount of HF was determined by weight difference, and was found to be 0.97 g (48 mmol).

The reactor was cooled again with liquid nitrogen, and inside it AsF: (10.0 mmol) was condensed by static vacuum, through a Pyrex-glass manifold.

The reactor was heated again to $23°$ C., while being gently stirred in order to mix HF and $AsF_5$.

After again cooling the reactor down to $-196°$ C., the above perfluorinated oxazetidine (XVIII) (5.00 mmol) was condensed under static volume, again through a glass vacuum line.

The mixture was heated with stirring to room temperature; a vigorous reaction started as soon as the mixture began to melt. The reaction was allowed to proceed at the temperature of 23° C. for 18 hours.

The reactor was then degassed by pumping off the non-condensible gases at −196° C.; this operation makes easier the subsequent step of vacuum transfer.

After degassing at the temperature of −196° C., the reaction mixture was heated to 23° C., and the volatile matters were condensed via static vacuum, through a stainless-steel manifold, inside a reaction bomb cooled with liquid nitrogen (having a capacity of 150 mol, equipped with a stainless-steel valve), containing 12.22 g (291 mmol) of NaF powder, in order to remove HF and $AsF_5$, and containing several stainless-steel balls having a diameter of ⅜". Some heating of the reactor (about 100° C.), as well as a stirring for about 20 minutes, allow the components to transfer into the bomb.

After 2.5 hours at the temperature of 23° C., with intermittent shaking, any volatiles contained inside the reaction bomb were slowly pumped into a Pyrex "U"-trap, cooled with liquid nitrogen. The following fractionation under dynamic vacuum of this material, through a train of "U"-traps cooled at −70° C., at −95° C. and at −196° C., yields 4.84 mmol of

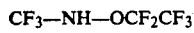

$CF_3$—NH—$OCF_2CF_3$ inside the trap at −95° C. [yield 96.8%, as computed relative to oxazetidine (XVIII)].

$CF_3$—NH—$OCF_2CF_3$ was characterized as follows:
IR (3 torr): 3342 ($\tau$N-H,m); 1483 (sh,w); 1453 (s); 1399 (w); 1313 (vs); 1275 sh,m); 1236 (vs); 1197 (vs); 1170 (vs); 1107 (vs); 1028 (w); 969 (w); 919(m); 863 (m); 814 (w); 741 (m); 679 (w); 620 (w); 569 (w) cm$^{-1}$: wherein m=medium; sh=shoulder, w=weak; s=strong and vs=very strong.

NMR: $CF_3{}^A N(H)$—$OCF_2{}^B CF_3{}^C$ δ $^1$H (CDCl$_3$) 6.6 (br, q); $^{19}$F(CDCl$_3$) A −70.6 (3F, d-t); B −95.3 (2F, q-q); C −84.9 ppm (3F, t); $J_{HA}$=3.6; $J_{AB}$=3.8; $J_{BC}$=1.7; $J_{HB}$=$J_{HC}$=$J_{AC}$=0Hz.

Mass spectrum: major m/z [EI]: 219 (M+); 200 (M-F+); 180 (M-F-HF+); 130 (M-HF-$CF_3$+); 119 ($CF_3CF_2$+); 69 ($CF_3$+); major m/z [CI]: 200 (M+1+); 200 (m+1-HF+); 180 (M+1-2HF+); 130 (M-HF-$CF_3$+); 119 ($CF_3CF_2$+).

EXAMPLE 2

This example illustrates the reaction:

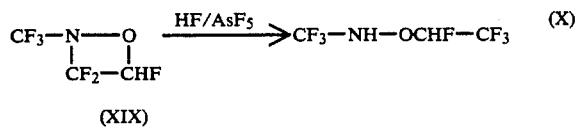

Oxazetidine (XIX) was prepared by thermal cycloaddition of $CF_3$—N=0 and $CF_2$=CHF (Banks, R.E. et al., J. Chem. Soc., 2506–2513, 1965).

The same general operating procedure as in Example 1 was followed, by using a reactor having an internal volume of about 35 ml.
The following materials were fed:
1.73 g of anhydrous HF (86 mmol);
10.00 mmol of $AsF_5$;
5.00 mmol of oxazetidine (XIX).

The mixture was heated with stirring to room temperature; a vigorous reaction started as soon as the mixture began to melt. The reaction was allowed to proceed at the temperature of 23° C. over 24 hours.

The neutralization was carried out with 18.16 g (432 mmol) of NaF powder.

During the vacuum fractionation, 3.20 mol of

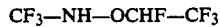

$CF_3$—NH—OCHF—$CF_3$ was obtained in a trap at −90° C. (yield 64.0%, as computed relative to oxazetidine).

$CF_3$—NH—OCHF—$CF_3$ was characterized as follows:
IR (3 torr): 3335 ($\tau$N-H,m); 2989 ($\tau$C-H,w); 1478 (sh,w); 1433 (s); 1409 (w); 1344 (w); 1291 (vs); 1214 (vs); 1191 (vs); 1127 (vs); 1008 (s); 1021(w); 989 (sh,w); 923 (m); 904 (m); 830 (w); 725 (m); 700 (m); 609 (w); 563 (w) cm$^{-1}$.

NMR: $CF_3{}^A N(H^B)$—$OCH^C F^D CF_3{}^E$ δ $^1$H (CDCl$_3$)B 6.7 (1H, br; q); C. 5.7 (1 H, d-q); δ $^{19}$F(CDCl$_3$)A −71.2 (3F, d-d); D −144.8 (1F, d-q-q); E −82.6 ppm (3F, d-d); $J_{AB}$=8.4; $J_{AD}$=2.2; $J_{CD}$=57.6; $J_{CE}$=3.2; $J_{DE}$=5.9; $J_{AC}$=$J_{AE}$=$J_{BC}$=$J_{BD}$=$J_{BE}$=0 Hz.

Mass spectrum: major m/z [EI]: 201 (M+); 182 (M-F+); 162 (M-F-HF+); 132 (M-$CF_3$+); 112 (M-$CF_3$-HF+); 101 ($CF_3$CFH); 100 ($CF_3CF_3$+); 69 ($CF_3$+); major m/z[CI]: 202 (M+1+); 182 (M+1-HF+).

EXAMPLE 3

This example illustrates the reaction:

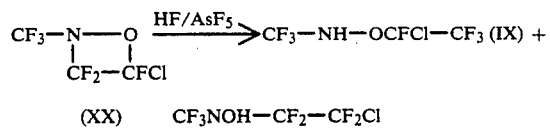

(XX)   $CF_3NOH$—$CF_2$—$CF_2Cl$

Oxazetidine (XX) was prepared from $CF_3$—N=0 and $CF_2$=CFCl (Barr, D. A. et al., J. Chem. Soc., 1961, 1351–1362).

The same general operating procedure as of Example 1 was followed, by using a reactor having an internal volume of about 18 ml.

The following materials were fed:
2.5 mmol of anhydrous HF (86 mmol);
3.7 mmol of $AsF_5$;
1.22 mmol of oxazetidine (XX).

The mixture was heated to 25° C. No reaction appeared to take place at once, but after a shaking for a time of about 5 minutes, the two liquid phases, initially immiscible, became homogeneous. The mixture was left standing at 25° C. for 18 hours.

The neutralization was carried out with 10.28 g (245 mmol) of NaF powder.

During the vacuum fractionation, a trap at the temperature of −60° C. collected 0.25 mmol of

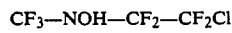

$CF_3$—NOH—$CF_2$—$CF_2Cl$ (yield 20%, as computed relative to oxazetidine), and a trap at −111° C. collected 0.78 mmol of

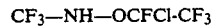

$CF_3$—NH—OCFCl-$CF_3$ (yield 64%).

The novel compound $CF_3$—NH—O—CFCl-$CF_3$ was characterized as follows:
IR (4 torr): 3333 (N-H,m); 1489 (sh,w); 1450 (s); 1336 (s); 1308 (vs); 1279 (sh,m); 1228 (vs); 1206 (sh,s); 1149

(s); 1126 (s); 1093 (vs); 1022 (m); 993 (s); 918 (m); 874 (w); 839 (m); 654 (w); b 563 (w) cm$^{-1}$.

NMR: $CF_3{}^A N(H^1)$—$OCF^B ClCF_3{}^C$ δ $^1H$ (CDCl$_3$) 6.6 (br, q); δ$^{19}$F(CDCl)$_3$ A −69.9 (3F, d-d); B −81.3 (1F,q-q); C −83.1 ppm (3F, d-m); $H_{HA}$=8.5; $J_{AB}$=4.1; $J_{BC}$=2.4; $J_{HB}$=$J_{HC}$=$J_{AC}$=0 Hz.

Spectrum: major m/z [EI]: 200 (M-Cl$^+$); 180 (M—Cl—HF$^+$); 135/137 (CFClCF$_3$); 85/87 (CF$_2$Cl$^+$); 69 (CF$_3{}^+$); major m/z [CI]: 236/238 (M+1); 216/218 (M+1—HF$^+$); 200 (M—Cl$^+$); 180 (M—Cl—HF$^+$); 135/137 (CFClCF$_3{}^+$).

EXAMPLE 4

This example illustrates the reaction:

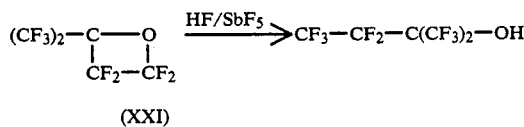

(XXI)

Oxethane (XXI) was prepared by means of the photochemical addition of hexafluoro-acetone and C$_2$F$_4$ (French patent No. 1,391,493).

The same general operating procedure as in Example 1 was followed, by using a reactor having an internal volume of 12 ml.

The following materials were fed:
2.06 g (9.55 mmol) of SbF$_5$;
2.21 g (110 mmol) of anhydrous HF;
9.55 mmol of oxethane (XXI).

The reactor was heated to 23° C. whereupon; the mixture formed two liquid phases with no evidence of reaction. The reactor was then heated up to the temperature of 55° C. over 17 hours after which time period the mixture had become homogeneous.

The neutralization was carried out with 23.19 g (553 mmol) of NaF powder.

The vacuum fractionation yielded 9.20 mmol of

inside a trap at the temperature of −80° C. (yield 96.3%, as computed relative to the oxethane).

EXAMPLE 5

This example illustrates the preparation of

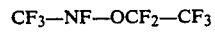

(XI) by fluorination of $CF_3$—$NH$—$OCF_2CF_3$.

All the process steps, carried out under vacuum, were accomplished under 5 microns Hg.

The reactor consisted of a stainless-steel reaction bomb of 150 ml of capacity, equipped with a stainless-steel valve, and previously passivated with 1 atm of F$_2$ for 18 hours, at the temperature of 23° C. The reaction bomb was put under vacuum, was cooled down to −196° C.; and

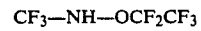

(2.50 mmol) was condensed under static vacuum through a Pyrexglass vacuum line.

F$_2$ was introduced into the reaction bomb, at the temperature of −196° C., through a vacuum line of stainless-steel; a 5% excess of F$_2$ was present (2.62 mmol of total F$_2$).

The liquid nitrogen was poured out from the Dewar bottle, and the reaction bomb was allowed to slowly warm inside the empty Dewar bottle. The temperature increased from −196° C. up to about +5° C. during 23.5 hours; at this time, the reaction bomb was cooled again down to −196° C., and a trace of unreacted F$_2$ was pumped off into the stainless-steel vacuum line.

After heating the reaction bomb to 23° C. the volatile matter was condensed via static vacuum through the stainless-steel manifold into a Hoke bomb of stainless-steel, cooled with liquid nitrogen, of 75 ml of capacity, containing 2.01 g (47.9 mmol) of NaF powder, in order to remove HF. The NaF-containing bomb had been equipped with a stainless-steel valve, and the bomb, already containing NaF, had been previously passivated with 1 atm of F$_2$ during a time of 6 hours, at the temperature of 23° C.

The volatile transferred matter was allowed to remain on NaF for 18 hours at the temperature of 23° C. The contents of the NaF-containing bomb were then carefully pumped out, and collected inside a "U"-shaped trap of Pyrex glass, cooled at −196° C. The fractionation under dynamic vacuum through a train of traps at the temperatures of −90° C., −135° C. and −196° C. yielded 2.46 mmol of

inside the trap at −135° C. (yield 98.4%, as computed relative to

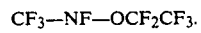

CF$_3$—NF—OCF$_2$CF$_3$ was characterized as follows:
IR (4 torr): 2304 (vw); 1400 (w); 1277 (vs); 1243 (vs); 1209 (sh,s); 1193 (vs); 1098 (vs); 998 (m); 932 (m); 889 (m); 826 (vw); 753 (w); 696 (m); 655 (w); 604 (vw); 531 (vw) cm$^{-1}$.

NMR $CF_3{}^C N(F^D)$—$OCF^A F^B CF_3{}^E$ $^{19}$F(CDCl$_3$, 23° C.) A −93.3 (1F, m); B −95.6 (1F, m); C −81.1 (3F, br s); D +10.5 (1F, br s); E −8484.9 ppm (3F, q); $J_{AB}$=142.1; $J_{AC}$=1.7; $J_{AD}$=5.2; $J_{AE}$=1.7; $J_{BD}$ =7.4; $J_{BE}$=1.7; $J_{CD}$=1.5; $J_{AE}$=1.6; $J_{BC}$=$J_{CE}$=0 Hz.

Mass spectrum: major m/z [EI]: 119 (C$_2$F$_5{}^+$); 69 (CF: ); 50 (CF$_2{}^+$); major m/z [CI]: 238 (M+1$^+$); 218 (M+1—HF$^+$); 130 (CF$_2$NOCF$_2{}^+$); 119 (C$_2$F$_5{}^+$).

EXAMPLE 6

This example illustrates the catalysts of C$_2$F$_4$ polymerization by using CF$_3$—NF—OCF$_2$CF$_3$.

C$_2$F$_4$ (PCR, Inc.) was washed, in order to remove from it its polymerization inhibitor (d-limonene, boiling point 178° C.), by being made to flow through a trap cooled at −111° C., under dynamic vacuum conditions; the no longer inhibited C$_2$F$_4$ was collected inside a trap having the temperature of −196° C. This operation, as well as all subsequent operations to be carried out under vacuum, were carried out under a vacuum of 5 microns Hg.

Inhibitor-free C$_2$F$_4$ (2.00 mmol) and CF$_3$—NF—OCF$_2$CF$_3$ (0.20 mmol) were condensed via static vacuum inside a Pyrex-glass tube cooled with liquid nitrogen; the tube had an internal volume of 48.8 ml, and was equipped with a glass/Teflon stopcock. The tube and its contents were allowed to warm up to the temperature of 23° C., and were heated, by using a heating tape, up to the temperature of 150° C., during a time of 12 hours.

After cooling to room temperature, and after removing the heating tape, the tube was found to contain a soft fluffy mass constituted by a solid of white color. The residual volatile matter was carefully pumped off and collected inside a liquid-nitrogen trap. No non-condensible gases were found. The PTFE remaining inside the reaction tube was found to weigh 140 mg, by weight difference, and represented 1.40 mmol, i.e., 70% of the original tetrafluoroethylene.

The fractionation of the residual volatile matter, by operating under dynamic vacuum conditions, through traps cooled at $-135°$ C. and at $-196°$ C., yielded 0.21 mmol of material inside the trap at $-135°$ C.; the IR spectrum of such a material showed that it was constituted by the catalyst $$CF_3-NF-OCF_2CF_3$$

(quantitative recovery).

The separator at $-196°$ C. contained 0.55 mmol of $C_2F_4$; i.e., 27.5% of the originally used olefin.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirir and scope of the appended claims. The above references are hereby incorporated by reference.

What is claimed is:

1. A process for the preparation of fluorinated compounds belonging to the classes:

$$XH-Y-CZ_1Z_2-(CF_2)_bF \quad (I)$$

and $$YH-X-(CF_2)_n-CZ_1Z_2F \quad (II)$$

wherein:
X is $NR_x$, O, S, $CFR_x$, $C(R_x)_2$, or $CF_2$;
Y is $NR_x$, O, S, $CFR_x$, $C(R_x)_2$, or $CF_2$;
X is different from Y;
$R_x$ is a perhalogenated alkyl group, containing from 1 to 4 carbon atoms;
n is either 0 or 1 with the proviso that when n=0, X=$NR_x$ and Y=O and when n=1, one of X and Y is $NR_2$;
$Z_1$ and $Z_2$ which may be equal to, or different from, each other, represent F, Cl, Br, H or $R_x$, comprising a fluorinated cyclic compound of the formula:

(III)

wherein X, Y, $R_x$, n, $Z_1$ and $Z_2$ have the above stated meanings, is reacted, at a temperature within the range of from $-80°$ to $+300°$ C., with HF in the presence of a Lewis acid.

2. A process according to claim 1, wherein the Lewis acid is selected from the group consisting of $AsF_5$, $SbF_5$, or $BF_3$.

3. A process according to claim 1 or 2, wherein at the end of the reaction, the Lewis acid and any excess HF are separated from the end product by neutralization with a neutralizing agent.

4. A process according to claim 1 or 2, wherein the reaction is carried out at a temperature within the range of from 0° to 100° C.

5. A process according to claim 1 or 2, wherein $R_x$ is a perfluorinated alkyl group.

6. A process according to claim 1 or 2, wherein the fluorinated cyclic compound has the formula:

(IV)

and the end products have the formulae:

$$R_x-NH-O-CZ_1Z_2-CF_3 \quad (V)$$

and $$R_x-NOH-CH_2-CZ_1Z_2F \quad (VI).$$

7. A process according to claim 1 or 2, wherein the fluorinated cyclic compound has the formula:

(XIV)

and the end product has the formula:

$$R_x-NH-O-CF_3 \quad (XV).$$

8. A process according to claim 1, wherein X and Y are selected from the group consisting of $NR_x$ or O.

* * * * *